United States Patent [19]

Payne

[11] Patent Number: 5,700,742
[45] Date of Patent: Dec. 23, 1997

[54] ANTIMICROBIAL TREATMENT OF TEXTILE MATERIALS

[75] Inventor: John David Payne, Rossendale, United Kingdom

[73] Assignee: Zeneca Limited, London, United Kingdom

[21] Appl. No.: 632,449

[22] PCT Filed: Oct. 7, 1994

[86] PCT No.: PCT/GB94/02194

§ 371 Date: Apr. 18, 1996

§ 102(e) Date: Apr. 18, 1996

[87] PCT Pub. No.: WO95/12021

PCT Pub. Date: May 4, 1995

[30] Foreign Application Priority Data

Oct. 27, 1993 [GB] United Kingdom ............... 9322132

[51] Int. Cl.$^6$ ........................................... D04H 1/58
[52] U.S. Cl. ........................................... 442/123; 442/153
[58] Field of Search ........................... 442/123, 153

[56] References Cited

U.S. PATENT DOCUMENTS 5,141,803  8/1992  Pregozen ........................ 428/288

FOREIGN PATENT DOCUMENTS

| | | |
|---|---|---|
| 698 595 | 11/1967 | Belgium . |
| 265 202 | 4/1988 | European Pat. Off. . |
| 485 079 | 5/1992 | European Pat. Off. . |
| 2 202 443 | 9/1988 | Germany . |
| 40 26 756 | 2/1992 | Germany . |
| 821 113 | 9/1959 | United Kingdom . |
| 2 187 097 | 9/1987 | United Kingdom . |

*Primary Examiner*—James J. Bell
*Attorney, Agent, or Firm*—Cushman Darby & Cushman IP Group Pillsbury Madison & Sutro LLP

[57] ABSTRACT

Antimicrobial treatment of textile material with an oligomeric or polymeric biguanide and a strong organic acid having a pK value below 4.5. Acid protects treated material against yellowing the presence of chlorine bleaches and loss of antimicrobial activity on laundering. The preferred biguanide is poly(hexamethylene biguanide) hydrochloride.

12 Claims, No Drawings

ANTIMICROBIAL TREATMENT OF TEXTILE MATERIALS

This application claims benefit of international application PCT/GB94/02184, filed Oct. 7, 1994.

The present invention relates to textile materials which are treated with a biguanide and a strong organic acid to prevent yellowing and loss of antimicrobial activity when subsequently laundered with an anionic detergent containing hypochlorite bleach.

It has been proposed to treat textile materials with poly(hexamethylene biguanide) in order to confer antimicrobial properties to the textile material as disclosed in EP 136 900.

Biguanides are particularly suited to application to textiles, especially cellulosic textiles and blends thereof, because of the substantivity which biguanides exhibit for such materials. However, such applications have not become commercially established where the treated material is to be subjected to laundering. There are two major reasons for this. Firstly, many commercially available detergents contain chlorine bleaching agents which react with the biguanide groups to produce a yellow discoloration and cause loss of antimicrobial protection. This is a particular disadvantage in white or pale coloured textiles. Secondly, many commercial detergents contain anionic surfactants which complex with the biguanide groups which often produce sticky deposits resulting in loss of "handle" and often impair the stain-release properties of the textile material. Also, following laundering, the textile material often exhibits an increase tendency to "tendering".

It has now been found that some or all of these deficiencies may be overcome by treating the textile material with a biguanide and an organic acid.

According to the invention, there is provided a method of treating a textile material to inhibit microbial growth which comprises applying to the textile material a) an oligo- or polymeric biguanide or the salt thereof with an inorganic acid or an organic acid having a pK value above 4.5 (hereafter "biguanide") and b) a strong organic acid having a pK value below 4.5 and free from any aliphatic or oxyalkylene chain containing 12 or more carbon atoms (hereafter "strong organic acid").

The biguanide which is used to treat the textile material contains at least two biguanide units of the formula (I):

and preferably from 2 to 100 such biguanide units.

Typically the biguanide units are linked by a bridging group which includes at least one methylene group. The bridging group may include a polymethylene chain which may optionally be interrupted by hetero atoms such as oxygen, sulphur or nitrogen. The bridging group may include one or more cyclic nuclei which may be saturated or unsaturated. It is generally preferred that the bridging group is such that there are at least three, and especially at least four, carbon atoms directly interposed between adjacent units of the formula (I). In general it is preferred that there are not more than ten carbon atoms and, especially not more than eight carbon atoms interposed between two adjacent units of the formula (I).

The terminal biguanide units may themselves be terminated by any suitable terminating group such as hydrocarbyl, substituted hydrocarbyl group, amino or amine hydrochloride or a group

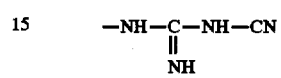

If the terminating group is hydrocarbyl this may be alkyl, cycloalkyl or aryl or a combination thereof, such as aralkyl. If the terminating group is substituted hydrocarbyl, the substituent or substituents can be any group or groups which do not have art undesirable adverse effect on the antimicrobial activity of the biguanide such as a hydrocarbyloxy, hydrocarbylcarbonyl (i.e. acyl), an ester (i.e. acyloxy), halogen atom or CN.

The biguanide may comprise a single species, especially where this is a dimer, or a mixture of species especially where it is polymeric and comprises a mixture of polymers having different chain lengths.

One preferred biguanide is a dimer which contains two units of the formula (I) linked by a polymethylene group, particularly a hexamethylene group. The terminating groups of preferred dimers are

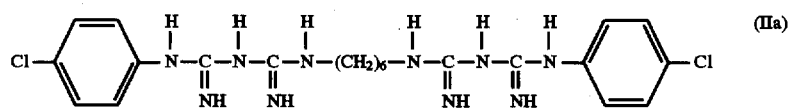

4-chlorophenyl or 2-ethylhexyl, for example as in the compound of formulae (IIa) and IIb, respectively

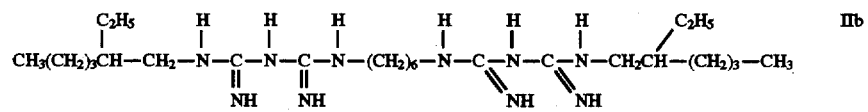

Another preferred biguanide comprises a mixture of polymeric biguanides, especially a mixture of linear polymeric biguanides with a recurring polymer unit represented by the formula

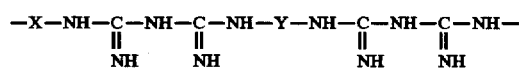

wherein X and Y may be the same or different and represent bridging groups in which the total number of carbon atoms directly interposed between the pairs of nitrogen atoms linked by X and Y is at least 9 and not more than 17.

The bridging groups X and Y may be polymethylene chains, optionally interrupted by hetero atoms such as oxygen, sulphur or nitrogen. X and Y may also incorporate cyclic nuclei which may be saturated or unsaturated, in which case the number of carbon atoms directly interposed between the pairs of nitrogen atoms linked by X and Y is taken as including the shortest segment or segments of the cyclic group or groups. Thus, the number of carbon atoms directly interposed between the nitrogen atoms in the group

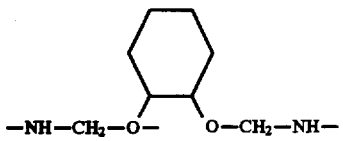

is 4 and not 8.

The preferred biguanide for use in the present invention is poly(hexamethylene biguanide), in which X and Y both represent the —(CH$_2$)$_6$— group.

The mixture of polymeric biguanides may be prepared by the methods described in UK Patent Specification Nos. 702,268 and 1,152,243 respectively, and any of the biguanide species or mixtures thereof described therein may be used as the biguanide in the present invention.

The polymeric biguanides may be terminated by an amine hydrochloride group or by an

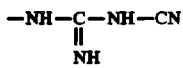

group, and the terminating groups on each polymer chain may be the same or different.

In any mixture of polymeric biguanides the number of individual biguanide units, i.e.

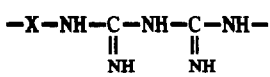

or

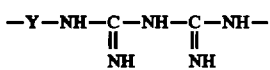

is preferably from 3 to about 80.

A preferred biguanide is a mixture of poly(hexamethylene biguanides) of formula III in the form of their hydrochloride salts.

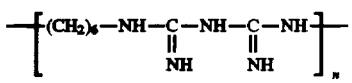

wherein n is from 4 to 15. The average molecular weight of this mixture of polymeric biguanides is from about 1100 to about 3300.

A preferred mixture of polymeric biguanides is available as an aqueous concentrate supplied as VANTOCIL IB (ZENECA Ltd). Poly(hexamethylene biguanide) hydrochloride is hereinafter referred to as PHMB.

The biguanide is preferably applied to the textile material as a salt of an inorganic acid or weak organic acid having a pK value above 4.5 (hereafter "weak organic acid"), especially a monobasic inorganic or weak organic acid. Examples of inorganic acids are hydrohalic acids such as the hydrobromic acid and especially hydrochloric acid. Examples of weak organic acids are acetic and propionic acids.

The strong organic acid may itself have antimicrobial activity, but this is not essential to the working of the invention. It may be a sulphonic acid or a sulphate but is preferably a carboxylic acid. The organic acid may contain more than one acid group such as in di- and tri-carboxylic acids and polymers and co-polymers derived from acrylic and methacrylic acid.

The strong organic acid may be substituted or unsubstituted. When it is substituted, the substituent or substituents may be any atom or group which reduces the pK value relative to the unsubstituted acid provided that such atom or group does not significantly affect the antimicrobial properties of the treated textile material and that it provides the required resistance to laundering. In the context of the invention, sulphamic acid is to be regarded as a strong organic acid.

Preferred strong organic acids are those containing 2 or 3 carboxylic acid groups.

The strong organic acid is essentially devoid of surface active properties and has little or no detergency properties. It is also essentially non-foaming.

The strong organic acid preferably has a pK value less than 4.0, more preferably less than 3.5 and especially from 3.1 to 0.5.

The acid group or groups of the strong organic acid are preferably —COOH, —CSOH or —COSH although in the following generic formulae IV, V and VI such groups are represented as —COOH for convenience. It is preferred that each acidic group is carboxy i.e. —COOH.

One preferred strong organic acid has the formula IV

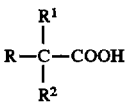

wherein

R is halogen, $C_{1-6}$-alkyl, $C_{1-6}$-alkenyl, substituted $C_{1-6}$-alkyl, phenyl, substituted phenyl, nitrile, carboxy, a group OR$^3$ or a group R$^3$CO.

R$^1$ and R$^2$ are, independently, hydrogen, halogen, amino, substituted amino, hydroxy, $C_{1-6}$-alkyl, substituted $C_{1-6}$-alkyl or R and R$^1$ together with the carbon atom to which they are attached form an alicyclic or heterocyclic ring; and R$^3$ is $C_{1-6}$-alkyl, substituted $C_{1-6}$-alkyl, phenyl or substituted phenyl; provided that R, R$^1$ and R$^2$ are selected to give a pK value below 4.5.

Another preferred strong organic acid has the formula V

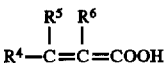

wherein

R$^4$ is hydrogen, $C_{1-6}$-alkyl, substituted $C_{1-6}$-alkyl $C_{1-6}$-alkenyl, phenyl substituted phenyl or —COOH; and R$^5$ and R$^6$ are, independently, hydrogen, $C_{1-4}$-alkyl or substituted $C_{1-4}$-alkyl.

A further preferred strong organic acid has formula VI

wherein

R$^7$ is phenyl, substituted phenyl or the group —COOH.

When R, R$^1$ or R$^2$ is halogen, it is preferably iodine, fluorine, bromine or more especially chlorine.

When R, R$^1$, R$^2$ or R$^3$ is alkyl, it may be linear or branched, but is preferably linear.

When R to R$^6$ is substituted alkyl, the substituent or substituents is preferably hydroxy, halogen, amino, substituted amino, nitrile, carboxy or $R^8CO-$ where $R^8$ is $C_{1-4}$-alkyl or phenyl.

When $R^1$ or $R^2$ is substituted amino, the substituent is preferably $C_{1-4}$-alkyl or the group $R^8-CO$.

When R, $R^3$, $R^4$ or $R^7$ is substituted phenyl, the substituent is preferably $C_{1-4}$-alkyl, hydroxy, halogen, nitro or —COOH.

When R and $R^1$ together with the carbon atom to which they are attached form an alicyclic ring, it is preferably cyclohexyl or cyclopropyl.

When R and $R^1$ together with the carbon atom to which they are attached form a heterocyclic ring, it is preferably furanyl.

Examples of the strong organic acid of formula IV wherein $R^1$ is amino or substituted amino are aspartic acid, leucine, phenylalanine and hippuric acid.

Organic acids of formula IV which have been found particularly useful are those containing two or more carboxylic acid groups, especially those also containing one or two hydroxy groups i.e. wherein one or both of $R^1$ and $R^2$ is hydroxy. Examples of such acids are adipic, butane tetracarboxylic, citric, dihydroxymalic, dihydroxytartaric, dimethylmalic, dimethylmalonic, glutaric, itaconic, malic, malonic, methylglutaric, methylmalonic, methylsuccinic, suberic, succinic, tartronic and tartaric acid.

Examples of monocarboxylic organic acids of formula IV are acetoacetic, ascorbic, bromoacetic, chloroacetic, chlorobutyric, chlorophenoxyacetic, chlorophenylacetic, chloropropionic, cyanoacetic, cyanophenoxyacetic, cyanopropionic, dichloroacetic, dichloroacetylacetic, diphenylacetic, ethylphenylacetic, glycolic, hydroxypropionic, iodoacetic, lactic, mandelic, nitrophenylacetic, nitrophenylpropionic, phenylacetic, phenylpropionic, trichloroacetic and vinylacetic acid.

Examples of organic acids of formula IV where R and $R^1$ form an alicyclic ring are cyclohexane-1,1-dicarboxylic and cyclopropane-1,1-dicarboxylic acids.

Examples of organic acids of formula V are acrylic, chlorocinnamic, fumaric, maleic, mesaconic, methylcinnamic and sorbic acid.

Examples of acids of formula VI are benzoic, bromobenzoic, chlorobenzoic, dihydroxybenzoic, ethylbenzoic, hydroxybenzoic, iodobenzoic, trimethylbenzoic, o-phenylbenzoic, phthalic, isopropylbenzoic, terephthalic, toluic acid and oxalic acid.

Examples of thiocarboxylic acids are thioacetic, thiomalic, thioglycolic and thiolactic acids.

Particularly useful effects have been obtained with citric, maleic, malonic and especially oxalic acids.

The textile material may be of natural or synthetic fibres including blends thereof. Thus, it may be cellulose, including viscose rayon and regenerated viscose rayon, wool, acrylic, polyamide such as nylon, polyester such as polyethyleneglycolterephthalate or polyurethane. It is, however, preferably cellulose or blends thereof.

The textile material may be woven or knitted or may be in the form of dry or wet laid fibres. It may be in the form of sheets, webs, threads or ready made up garments such as drapes, shirting, toweling, underwear, socks and sheeting. The textile material is especially that which may become soiled and prevalent to microbiological growth thus giving rise to objectionable odours or to health/hygiene problems.

The biguanide may be the only antimicrobial agent applied to the textile material or a mixture of such biguanides may be used. Other antimicrobial agents may also be included to improve the spectrum of microbiological protection provided that such other antimicrobial agent does not significantly interfere with the improved resistance of the treated textile material to laundering.

The textile material may also contain other textile processing adjuvants such as binders or resins, especially phenolformaldehyde or urea-glyoxal resins which are commonly used in the trade to impart crease-resistance and "easy care" properties to the textile material.

The biguanide is preferably applied to the textile material before the strong organic acid is applied. The biguanide and strong organic acid my be applied by any process common to the textile imdustry which is appropriate to the actual textile material. Thus, application may be by batch or substantive exhaustion, padding, dipping or spraying. Where appropriate, the textile material may be dried after application of the biguanide and prior to the application of the strong organic acid. The textile material may be white or coloured with either dyestuffs or pigments. It may contain other textile adjuvants commonly used in textile finishing processes such as brightening agents and softeners.

Since the biguanide in the form of a salt with an inorganic acid or weak organic acid is water soluble, the biguanide is preferably applied from aqueous solution. However, the solution of biguanide may contain other hydrophilic compounds or co-solvents such as ethanol. Similarly, the strong organic acid is also preferably applied from aqueous solution either in the form of the free carboxylic acid or in the form of a water-soluble salt, especially alkali metal salt such as lithium, sodium or potassium salt or as an ammonium salt.

The amount of biguanide which is applied to the textile material may be just sufficient to confer an antimicrobial effect to the material but is preferably in excess of this amount. Generally, the amount of biguanide is up to 2% preferably up to 1%, more preferably up to 0.5% and especially up to 0.1% by weight of the textile material. Good antimicrobial effects have been obtained with up to 0.01% by weight of textile material.

For convenience, an excess of the strong organic acid is applied so that those biguanide groups which are not required to bind with the textile material are blocked by the strong organic acid. Any excess of the acid may be removed by rinsing with water, but this is generally not necessary. It is particularly preferred that the amount of strong organic acid is just sufficient to form a salt with all the biguanide groups not required to bind with the textile material.

The textile material containing the biguanide which has been treated with the strong organic acid shows reduced tendency to discolour when exposed to a chlorine-containing bleach and also retains antimicrobial activity after washing with an anionic detergent. It has been found that certain textile materials, especially cellulosic materials retain antimicrobiological activity even after repeated laundering cycles. In addition, the textile materials treated according to the invention retain similar "handle" and "soil-release" characteristics after laundering compared with that of the untreated material.

Thus, as a further aspect of the invention there is provided a textile material treated with an oligo- or polymeric biguanide and a strong organic acid having a pK value below 4.5 and free from any aliphatic or oxyalkylene chains containing more than 12 carbon atoms. Some of the salts formed on the textile material are believed novel. Thus, as a still further aspect of the invention there is provided a salt of poly (hexamethylene biguanide) and a strong organic acid having a pK below 4.5 and free from any aliphatic or oxyalkylene chains containing more than 12 carbon atoms.

The invention is now further described with reference to the following examples where the amounts are expressed as parts by weight unless expressed to the contrary.

EXAMPLES 1 TO 17

These examples illustrate the protection against yellowing.

5 cm$^2$ squares of white cotton woven cloth (0.25 parts) were immersed in a 0.1% aqueous solution of PHMB for 5 minutes at 20°–25° C. The cotton was then removed and rinsed thoroughly with water. The treated cotton was then immersed in a 1% aqueous solution of a strong organic acid for 5 minutes at 20°–25° C. and again removed, squeezed and rinsed with water. The cotton pieces were finally immersed in a 3% aqueous solution of sodium hypochlorite at 40° C. for 1 hr. Again the cotton pieces were squeezed and thoroughly rinsed in water before drying.

The colour of these samples was assessed visually by measuring the colour with a Macbeth Reflectance Spectrophotometer. The results are given in Table I below.

TABLE 1

| Example a Comp Ex | Organic Acid | pK | Whiteness (a) % |
|---|---|---|---|
| 1 | citric | 2.9 | 100 |
| 2 | lactic | 3.7 | 97.0 |
| 3 | glycolic | 3.6 | 98.7 |
| 4 | thioglycolic | 3.4 | 99.9 |
| 5 | thiolactic | 3.5 | 99.6 |
| 6 | ethoxyacetic | 3.5 | 98.5 |
| 7 | chloroacetic | 2.7 | 101.9 |
| 8 | tartaric | 2.8 | 98.9 |
| 9 | malic | 3.2 | 97.6 |
| 10 | benzoic | 4.0 | ND |
| 11 | aspartic | 1.9 | 90.0 |
| 12 | phenylalanine | 2.2 | 89.7 |
| 13 | leucine | 2.4 | 89.5 |
| 14 | oxalic | 1.1 | 100 |
| 15 | malonic | 2.6 | 99.3 |
| 16 | maleic | 1.7 | 96.8 |
| 17 | btca | 3.4 | 99.8 |
| A | acetic | 4.5 | yellow |
| B | 2-hydroxybutyric | 4.7 | yellow |
| C | 3-hydroxybutyric | 4.72 | yellow |
| D | 4-hydroxybutyric | 4.72 | yellow |
| E | boric | — | yellow |
| Control | — | — | 73 |

Footnote to Table
btca is butane tetracarboxylic acid
a) Whiteness is measured as percent reflectance against a piece of untreated cotton.
ND is not determined.

EXAMPLE 18

This illustrates the antimicrobial properties of treated cotton.

A phosphate buffer as prepared by mixing aqueous solutions of 0.2 mol/liter Na$_2$HPO$_4$ (72 ml) and 0.2 mol/liter NaH$_2$PO$_4$ (28 mls), adding NaCl (5 parts) and diluting to 1 liter with distilled water. This buffer solution was sterilised by heating at 121° C. for 15 minutes.

A 24 hour shaken culture of Staphylococcus aureus (ATCC 6538P) was prepared at 37° C. The cell concentration was measured using a haemocytometer and the culture diluted with the phosphate buffer solution to give a concentration of between 5E5 and 3E5 cfu/ml (E is logarithmic power to base 10).

Samples of cotton cloth (0.2 parts) to be tested were placed in a screw-necked flask, inoculated with 0.2 ml of the bacterial culture, and the flask sealed and incubated at 37° C. for 18 hours.

After incubation, 20 mls of the phosphate buffer solution were added and the flask shaken for about 1 minute. The concentration of surviving cells in the buffer solution was then determined by a standard serial dilution technique on nutrient agar after 24 hour incubation at 37° C. The results are detailed in Table 2 for cotton samples treated with citric acid alone, PHMB alone and both citric acid and PHMB both with and without bleach. The treatment with citric acid, PHMB and bleach is as described in Example 1. The results show that citric acid prevents yellowing but exhibits poor antimicrobial activity and that the combination of citric acid and PHMB retains antimicrobial activity and also protects against yellow discoloration in the presence of hypochlorite bleach.

TABLE 2

| Example or Comp Ex | biguanide | organic acid | bleach | Appearance | Surviving bacteria |
|---|---|---|---|---|---|
| Control | none | none | no | white | 6E3 |
| F | none | none | yes | white | 7E3 |
| G | none | 1% citric | no | white | 6E2 |
| H | 0.01% PHMB | none | yes | yellow | 0 |
| 18 | 0.01% PHMB | 1% citric | yes | white | 0 |

EXAMPLE 19

This example illustrates the durability of the antimicrobial activity to repeated laundering. Samples of polyester/cotton (65/35) woven material were treated and tested as in Example 18 after five repeated washes for 50 minutes at 45° C. in a 0.2% w/w aqueous solution of sodium alkylethoxysulphonate. In this example, bleaching in the 3% aqueous solution of sodium hypochlorite was carried out for 20 minutes at 20°–25° C. The results are given in Table 3 which shows that the polyester/cotton material withstands discolouration in the presence of bleach and retains microbiological activity even after 5 laundering cycles in the presence of an anionic surfactant.

TABLE 3

| Example | Treatment | Surviving cells after 5 laundering | whiteness (%) |
|---|---|---|---|
| Control | none | 3E7 | 89 |
| I | 2% PHMB | 6E2 | 80 |
| 19 | 2% PHMB + 1% citric | 0 | 88 |

EXAMPLE 20

Example 14 was repeated execept that the cotton cloth was replaced by the same amount of a 35/65 cotton/polyethylene glycol terephthalate blend woven piece and the oxalic acid solution was 0.5% by weight. The results are given in Table 4 below.

TABLE 4

| Example | Treatment | Appearance | Whiteness (%) |
|---|---|---|---|
| 20 | 0.1% PHMB/0.5% oxalic acid | white | 80.99 |
| J | 0.1% PHMB | yellow | 70.69 |
| Control | | white | 81.9 |

EXAMPLE 21

White cotton woven pieces (250 parts) was immersed in a 0.1% aqueous solution of PHMB for 5 minutes at 20°–25°

C. The cotton piece was then removed and rinsed thoroughly with water. The treated cotton was then immersed in 0.5% aqueous solution of oxalic acid for 5 minutes at 20°–25° C. and again removed, squeezed, rinsed with water and dried. The cotton was then padded with a 0.2% solution of a glycoluril resin containing an acid catalyst, squeezed through a pair of nip rollers to give 60% pick-up and finally dried and baked for 10 minutes at 140° C. to cure the resin.

A similar cotton woven piece was prepared but omitting the oxalic acid treatment. A length of untreated cotton was used as control.

5 cm² squares of the above cotton cloths (0.25 parts) were treated with sodium hypochlorite as described in Example 14 and the antimicrobial properties were assessed as described in Example 18. The results are given in Table 5 below after subjecting to 0, 5 and 10 washing cycles as described in Example 19.

TABLE 5

| Example | Treatment | No. of Washes | Whiteness (%) | Surviving bacteria |
|---|---|---|---|---|
| 21 | 0.1% PHMB | 0 | 109 | 0 |
|  | 0.5% oxalic acid | 5 | 116 | 0 |
|  | 0.2% glycoluril | 10 | 126 | 0 |
| K | 0.1% PHMB | 0 | 84.3 | 0 |
|  | 0.2% glycoluril | 5 | 91.6 | 3.4 E2 |
|  |  | 10 | 101.9 | 1.7 E2 |
| Control | None | 0 | 97.4 | 4.3 E2 |

EXAMPLES 22 TO 24

White 35/65 cotton/polyethylene glycol terephthalate woven pieces (250 parts) were immersed in an aqueous solution of 0.4% PHMB for 5 minutes at 20°–25° C. They were then removed, squeezed, rinsed in water and dried. Half of the pieces were then immersed in a 2% aqueous solution of citric acid for 5 minutes at 20°–25° C. and again removed, squeezed and rinsed in water.

After drying the treated pieces were padded through a 1% aqueous bath of a curable resin, squeezed between nip rollers to give 60% up take, dried and baked for 10 minutes at 140° C.

The treated fabrics were then immersed in sodium hydrochlorite as described in Example 1. The protection against yellowing conferred by the citric acid is recorded in Table 6 below.

TABLE 6

| Example | Treatment | Citric Acid | Whiteness (%) |
|---|---|---|---|
| Control | — | — | 90 |
| L | 0.4% PHMB | — | 82 |
| M | 0.4% PHMB 1% epoxy resin | — | 82 |
| 22 | 0.4% PHMB 1% epoxy resin | 2% | 90 |
| O | 0.4% PHMB 1% melamine resin | — | 85 |
| 23 | 0.4% PHMB 1% melamine resin | 2% | 88 |
| P | 0.4% PHMB 1% urethane resin | — | 85 |
| 24 | 0.4% PHMB 1% urethane resin | 2% | 90 |

EXAMPLE 25

Example 15 was repeated except that the PHMB was replaced by the same amount of chlorohexidine digluconate and the strong organic acid used was a 0.5% aqueous solution of malonic acid. The results are given in Table 7 below.

TABLE 7

| Example | Treatment | Whiteness (%) |
|---|---|---|
| 25 | 0.1% chlorhexidine 0.5% malonic acid | 83 |
| Q | 0.1% chlorhexidine | 10.9 |
| Control | — | 97.1 |

I claim:

1. A method of treating a textile material to inhibit microbial growth which comprises applying to the textile material a) an oligo- or polymeric biguanide or salt thereof with an inorganic acid or an organic acid having a pK value above 4.5 followed by b) a strong organic acid having a pK value below 4.5 and free from any aliphatic or oxyalkylene chain containing 12 or more carbon atoms.

2. A method according to claim 1 wherein the strong organic acid has a pK value from 3.1 to 0.5.

3. A method according to either claim 1 or claim 2 wherein the biguanide contains at least two biguanide units of formula

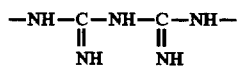

4. A method according to claim 3 wherein the biguanide is a compound of formula IIa or IIb or III

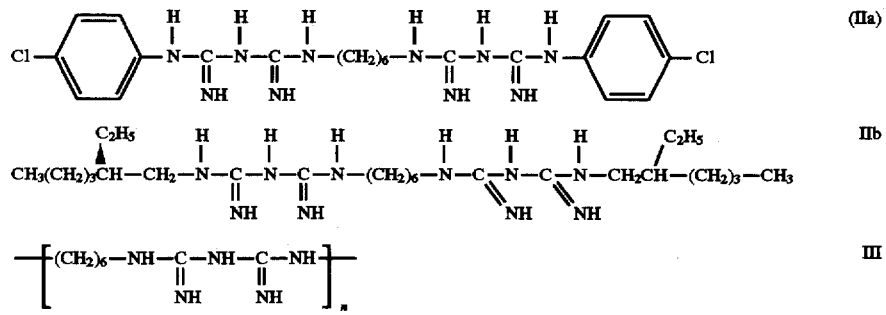

wherein n is 4 to 15.

5. A method according to claim 1 wherein the strong organic acid has the formula IV

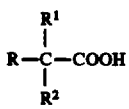   IV wherein

R is halogen, $C_{1-6}$-alkyl, $C_{1-6}$-alkenyl, substituted $C_{1-6}$-alkyl, phenyl, substituted phenyl, nitrile, carboxy, a group $OR^3$ or a group $R^3CO$;

$R^1$ and $R^2$ are, independently, hydrogen, halogen, amino, substituted amino, hydroxy, $C_{1-6}$-alkyl, substituted $C_{1-6}$-alkyl or R and $R^1$ together with the carbon atom to which they are attached form an alicyclic or heterocyclic ring; and $R^3$ is $C_{1-6}$-alkyl, substituted $C_{1-6}$-alkyl, phenyl or substituted phenyl;

provided that R, $R^1$ and $R^2$ are selected to give a pK value below 4.5.

6. A method according to claim 1 wherein the strong organic acid has the formula V

   V wherein $R^4$ is hydrogen, $C_{1-6}$-alkyl, substituted $C_{1-6}$ alkyl, $C_{1-6}$-alkenyl, phenyl, substituted phenyl or —COOH; and $R^5$ and $R^6$ are, independently, hydrogen, $C_{1-4}$-alkyl or substituted $C_{1-4}$-alkyl.

7. A method according to any one of claims 1 to 4 wherein the strong organic acid has the formula VI

   VI wherein $R^7$ is phenyl, substituted phenyl or the group —COOH.

8. A method as claimed in claim 1 wherein the acid is malonic, maleic, citric or oxalic acid.

9. A method as claimed in claim 1 wherein the textile material is rinsed with water after treatment with the strong organic acid.

10. A method as claimed in claim 1 wherein the textile material is cellulose or a blend thereof.

11. A method as claimed in any one of claims 1 to 10 wherein the textile material contains a binder or resin.

12. A textile material treated with a) an oligo- or polymeric biguanide or salt thereof with an inorganic acid or an organic acid having a pK value above 4.5 followed by b) a strong organic acid having a pK value below 4.5 and free from any aliphatic or oxyalkylene chain containing 12 or more carbon atoms.

* * * * *